(12) United States Patent
Standke et al.

(10) Patent No.: US 6,491,838 B1
(45) Date of Patent: Dec. 10, 2002

(54) TRIAMINO- AND FLUOROALKYL-FUNCTIONAL ORGANOSILOXANES

(75) Inventors: Burkhard Standke, Lörrach (DE); Michael Horn, Rheinfelden (DE); Peter Jenkner, Rheinfelden (DE); Jaroslaw Monkiewicz, Rheinfelden (DE)

(73) Assignee: Degussa AG, Duesseldorf (DE)

( * ) Notice: Subject to any disclaimer, the term of this patent is extended or adjusted under 35 U.S.C. 154(b) by 15 days.

(21) Appl. No.: 09/712,224

(22) Filed: Nov. 15, 2000

(30) Foreign Application Priority Data

Nov. 15, 1999 (DE) .......................... 199 55 047

(51) Int. Cl.⁷ .......................... C14C 9/00; C08G 77/26; C08G 77/24; C09D 183/08
(52) U.S. Cl. .......................... 252/8.57; 8/94.14; 106/2; 106/18.32; 106/287.11; 106/287.13; 106/287.15; 528/29; 528/31; 528/34; 528/38
(58) Field of Search .......................... 106/287.11, 287.13, 106/287.15, 2, 18.32; 252/8.57; 8/94.14; 528/29, 31, 34, 38

(56) References Cited

U.S. PATENT DOCUMENTS

| | | | | |
|---|---|---|---|---|
| 3,013,066 A | | 12/1961 | Alderson ..................... 502/230 |
| 5,000,861 A | * | 3/1991 | Yang .......................... 252/8.62 |
| 5,227,111 A | * | 7/1993 | Brangers et al. ............. 264/101 |
| 5,679,147 A | | 10/1997 | Standke et al. ......... 106/287.11 |
| 5,808,125 A | * | 9/1998 | Standke et al. ............. 556/424 |
| 5,863,509 A | | 1/1999 | Standke et al. ............. 427/221 |
| 6,054,601 A | * | 4/2000 | Standke et al. .......... 106/287.1 |
| 6,255,513 B1 | * | 7/2001 | Standke et al. ............. 427/445 |

FOREIGN PATENT DOCUMENTS

| | | |
|---|---|---|
| DE | 834 002 | 3/1952 |
| DE | 1 518 551 | 2/1969 |
| DE | 31 00 555 | 11/1981 |
| DE | 34 47 636 | 7/1986 |
| DE | 195 44 763 | 6/1997 |
| EP | 0 242 798 | 10/1987 |
| EP | 0 382 557 | 8/1990 |
| EP | 0 493 747 | 7/1992 |
| EP | 0 587 667 | 3/1994 |
| EP | 0 738 771 | 10/1996 |
| EP | 0 846 716 | 6/1998 |
| EP | 0 846 717 | 6/1998 |
| EP | 0 846 717 A2 | 6/1998 |
| EP | 0 902 969 | 3/1999 |
| GB | 935380 | 9/1963 |
| WO | WO 95/23804 | 9/1995 |
| WO | WO 95/23830 | 9/1995 |
| WO | WO 96/06895 | 3/1996 |
| WO | WO 97/23432 | 7/1997 |

* cited by examiner

*Primary Examiner*—Anthony J. Green
(74) *Attorney, Agent, or Firm*—Oblon, Spivak, McClelland, Maier & Neustadt, P.C.

(57) ABSTRACT

An organosiloxane which has at least one triamino group of formula I:

$$[NH_x(CH_2)_aNH_y(CH_2)_bNH_z]— \qquad (I)$$

which is bonded to at least one silicon atom via at least one N-bonded alkylene group having 1 to 4 C atoms, a and b are identical or different and are each an integer ranging from 1 to 6, x is 0 or 1 or 2, y is 0 or 1, z is 0 or 1 or 2, with the proviso that $(x+y+z) \leq 4$, and at least one Si—C-bonded fluoroalkyl group of formula II:

$$F_3C(CF_2)_r(CH_2)_s— \qquad (II)$$

wherein r is 0 or an integer ranging from 1 to 18 and s is 0 or 2.

23 Claims, No Drawings

TRIAMINO- AND FLUOROALKYL-FUNCTIONAL ORGANOSILOXANES

BACKGROUND OF THE INVENTION

1. Field of the Invention

The present invention relates to triamino- and fluoroalkyl-functional organosiloxanes. More particularly, the present invention relates to a composition which comprises at least one aminoalkyl- and fluoroalkyl-functional organosiloxane containing hydroxyl groups and/or alkoxy groups, water, and optionally an alcohol and/or an acid. The present organosiloxanes contain hydroxyl groups and/or alkoxy groups and are formulated in aqueous compositions. The present organosiloxanes are completely or partially hydrolyzed, which is to say that they contain hydroxyl and/or alkoxy groups in the context of the equilibrium being established. The present invention furthermore relates to the preparation of the triamino- and fluoroalkyl-functional organosiloxanes and their use.

2. Description of the Background

Fluoroalkylalkoxysilanes and their corresponding polycondensates are well known, as well as their use as hydrophobicizing and olephobicizing agents, as described in, for example DE 834 002, U.S. Pat. No. 3,012,066, British Patent 935 380, DE 31 00 555, EP 0 382 557, EP 0 493 747, EP 0 587 667 and DE 195 44 763.

Fluoroalkylalkoxysilanes are usually not used in concentrated form, since they are extremely expensive products. Furthermore, fluoroalkylalkoxysilanes are not soluble in water.

In order to prepare sufficiently stable solutions or formulations of fluoroalkyl functional silanes and corresponding cocondensates, organic solvents or emulsifiers have been employed as described in, for example DE 34 47 636, DE 36 13 384, WO 95/23830, WO 95/23804, WO 96/06895, WO 97/23432 and EP 0 846 716.

A disadvantage of solvent- and emulsifier-containing formulations and of organosiloxanes with a high content of alkoxy groups is the fact that such systems are undesirable on ecological and work safety grounds. Efforts have, therefore, increasingly been made to provide water-based systems with the lowest possible content of volatile organic compounds (abbreviation: "VOC").

Nitrogen-containing and aminoalkyl- and fluoroalkyl-functional organosiloxanes which are substantially free of alkoxy groups are known as water-soluble constituents in otherwise emulsifier- and surfactant-free compositions for rendering surfaces water-, oil- and dirt-repellent as described in DE 15 18 551, EP 0 738 771 and EP 0 846 717).

A relatively high content of aminoalkyl groups must always be used in the water-based systems mentioned in order to ensure a good solubility in water. On the other hand, a high content of aminoalkyl groups is counterproductive, since these groups have hydrophilic properties and, therefore, counteract the efforts to provide a system which, as far as possible, exhibits hydrophobic properties. A need continues to exist for water-soluble aminoalkyl- and fluoroalkyl-functional organosiloxanes, but which retain hydrophobic properties.

SUMMARY OF THE INVENTION

Accordingly, one object of the present invention is to provide a water-soluble aminoalkyl- and fluoroalkyl-functional organosiloxane which has acceptable hydrophobic properties.

Another object of the present invention is to provide organosiloxanes which have the highest possible number of fluoroalkyl groups in relation to the number of aminoalkyl groups.

Briefly, these objects and other objects of the present invention as hereinafter will become more readily apparent can be attained by an organosiloxane which has at least one triamino group of formula I:

$$[NH_x(CH_2)_a NH_y(CH_2)_b NH_z]— \qquad (I)$$

wherein the group is bonded to at least one silicon atom via at least one N-bonded alkylene group having 1 to 4 C atoms, a and b are identical or different and are an integer ranging from 1 to 6, x is 0 or 1 or 2, y is 0 or 1, z is 0 or 1 or 2, with the proviso that $(x+y+z) \leq 4$, and at least one Si—C-bonded fluoroalkyl group of formula II:

$$F_3C(CF_2)_r(CH_2)_s— \qquad (II)$$

wherein r is 0 or an integer ranging from 1 to 18 and s is 0 or 2.

DETAILED DESCRIPTION OF THE PREFERRED EMBODIMENTS

It has now been found, surprisingly, that a low-viscosity, that is to say preferably a viscosity of <100 mPas, composition, which as a rule is clear to slightly opalescent and which is also outstandingly stable to storage for several months on dilution with water and comprises at least one water-soluble, triamino- and fluoroalkyl-functional organosiloxane containing hydroxyl groups and/or alkoxy groups or a mixture of corresponding organosiloxanes, water, and optionally a content of alcohol and/or a content of acid, can be prepared by i) mixing at least one aminoalkylalkoxysilane of formula IIIa:

$$NH_2(CH_2)_2NH(CH_2)_2NH(CH_2)_3Si(R')_j(OR)_{(3-j)} \qquad (IIIa)$$

wherein R and R' are identical or different and are a linear or branched alkyl group having 1 to 4 C atoms and j is 0 or 1, and/or of formula IIIb:

$$[NH_2(CH_2)_2]_2N(CH_2)_3Si(R')_k(OR)_{(3-k)} \qquad (IIIb)$$

wherein R and R' are identical or different and are a linear or branched alkyl group having 1 to 4 C atoms and k is 0 or 1, and/or a "bis-product" or a mixture of "bis-products" of formula IIIc:

$$[NH_x(CH_2)_a NH_y(CH_2)_b NH_z]\cdot[(CH_2)_c Si(R')_d(OR)_{(3-d)}]_e \qquad (IIIc)$$

wherein R and R' are identical or different and are a linear or branched alkyl group having 1 to 4 C atoms, a is an integer from 1 to 6, b is 1, 2, 3, 4, 5 or 6, c is 1, 2, 3 or 4, d is 0 or 1 e is 1, 2, 3, 4 or 5, x is 0 or 1 or 2, y is 0 or 1, z is 0 or 1 or 2, and with the proviso that $(x+y+z) \leq 4$, where e in the case where $(x+y+z)=0$ assumes the numerical value 5, for $(x+y+z)=1$ e=4, for $(x+y+z)=2$ e=3, for $(x+y+z)=3$ e=2, and in the case where $(x+y+z)=4$ e=1; and ii) at least one fluoroalkylalkoxysilane of formula IV:

$$F_3C(CF_2)_r(CH_2)_s Si(R'')_t(OR)_{(3-t)} \qquad (IV)$$

wherein r is 0 or an integer of 1 to 18, s is 0 or 2 and t is 0 or 1, and R and R" are identical or different and are a linear or branched alkyl group having 1 to 4 C atoms. Optionally, an alcohol, water and/or a water/alcohol mixture can be added to this material and also optionally, a catalyst. These materials are allowed to react or they are reacted. That is, these components may be pre-hydrolyzed or they may be hydrolyzed and are then subjected to cocondensation. The alcohol is completely or partly removed, that is to say suitably down to residual amounts of less than 5% by weight, and then optionally, adjusting the resulting product mixture to a pH of <12 by addition of an inorganic or organic acid. The composition suitably has a pH of <11.

The present composition moreover has the effect of further improved liquid-repellent properties of a correspondingly treated mineral surface—using both hydrophilic and hydrophobic standard test liquids (tests according to the "Teflon® specification test kit" from DuPont). Reference is made to the Examples here.

In particular, at a molar ratio of starting substances which are either an N-[N'-(2-aminoethyl)-2-aminoethyl]-3-aminopropyltrialkoxysilane or an aminoalkylalkoxysilane of formula IIb or formula IIIc, to a fluoroalkylalkoxysilane having formula IV of 1:≦3.5 preferably 1:3 to 1:0.5, particularly preferably 1:3 to 1:1, especially preferably 1:3 to 1:2, a particularly high fluoroalkyl group content can be achieved in the water-soluble cocondensates of the present invention.

The composition of the invention can be diluted with water in all proportions if desired. In the case of completely hydrolyzed systems, as a rule no additional alcohol, as a result of hydrolysis, is formed here. In general, compositions of the invention and dilute systems are outstandingly stable upon storage for more than 6 months.

The invention thus relates to a composition which comprises at least one organosiloxane containing hydroxyl groups and/or alkoxy groups and water, wherein the organosiloxane carries at least one triamino group of formula I:

  (I)

wherein the triamino group is bonded to at least one silicon atom via at least one N-bonded alkylene group having 1 to 4 C atoms, a and b are identical or different and are each an integer of 1 to 6, x is 0 or 1 or 2, y is 0 or 1, z is 0 or 1 or 2, and with the proviso that (x+y+z)≦4, and at least one Si—C-bonded fluoroalkyl group of formula II:

  (II)

wherein r is 0 or an integer of 1 to 18 and s is 0 or 2.

The invention also relates to organosiloxanes which contain at least one triamino group of formula I:

  (I)

wherein the triamino group is bonded to at least one silicon atom via at least one N-bonded alkylene group having 1 to 4 C atoms, a and b are identical or different and are each an integer of 1 to 6, x is 0 or 1 or 2, y is 0 or 1, z is 0 or 1 or 2, and with the proviso that (x+y+z)≦4, and at least one Si—C-bonded fluoroalkyl group of formula II:

  (II)

wherein r is 0 or an integer of 1 to 18 and s is 0 or 2.

Organosiloxanes of the invention are in general based on so-called [M], [D] and [T] structural units, which, as such, are familiar to the expert, it also being possible for the oligomeric and polymeric organosiloxane units to form aggregates. Such organosiloxanes usually carry hydroxyl groups and/or alkoxy groups as functional groups, in addition to the functional groups of the invention. The presence of hydroxyl and alkoxy groups can, as a rule, be controlled by the amount of water added during the preparation and the completeness of the removal of alcohol. Furthermore, the organosiloxanes of the invention can also contain, that is to say carry, alkyl groups having 1 to 16 C atoms as additional functional groups.

In particular, the organosiloxanes of the invention can be diluted with water in an outstanding manner. Low-viscosity, slightly opalescent liquids are in general obtained in this case. However, the organosiloxanes of the invention can also be dissolved in alcohol or incorporated into water-soluble emulsions.

Another aspect of the invention is a process for the preparation of an organosiloxane-containing composition, which comprises mixing i) at least one aminoalkylalkoxysilane of formula IIIa:

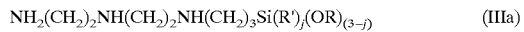  (IIIa)

wherein R and R' are identical or different and are each a linear or branched alkyl group having 1 to 4 C atoms and j is 0 or 1, and/or of formula IIIb:

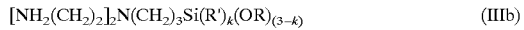  (IIIb)

wherein R and R' are identical or different and are a linear or branched alkyl group having 1 to 4 C atoms and k is 0 or 1, and/or a "bis-product" or a mixture of "bis-products" of formula IIIc:

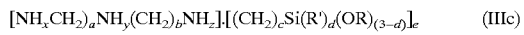  (IIIc)

wherein R and R' are identical or different and are a linear or branched alkyl group having 1 to 4 C atoms, a is an integer ranging from 1 to 6, b is 1, 2, 3, 4, 5 or 6, c is 1, 2, 3 or 4, d is 0, e is 1, 2, 3, 4 or 5, x is 0 or 1 or 2, y is 0 or 1, z is 0 or 1 or 2, and with the proviso that (x+y+z)≦4, where e in the case where (x+y+z)=0 assumes the numerical value 5, for (x+y+z)=1 e=4, for (x+y+z)=2 e=3, for (x+y+z)=3 e=2, and in the case where (x+y+z)=4 e=1, and ii) at least one fluoroalkylalkoxysilane of formula IV:

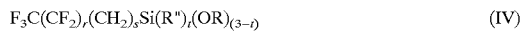  (IV)

wherein r is 0 or an integer ranging from 1 to 18, s is 0 or 2 and t is 0 or 1, and R and R" are identical or different and are each a linear or branched alkyl group having 1 to 4 C atoms, adding water or a water/alcohol mixture and, if appropriate a catalyst to the combined materials, allowing the components to react and completely or partly removing the alcohol. The product mixture thus obtained is brought to a pH of <12, preferably to 4 to 7 by addition of an inorganic or organic acid.

Still another aspect of the invention is a composition which is prepared by the process of the invention. The invention is also directed to triamino and fluoroalkyl-functional organosiloxanes the invention, in particular mixtures thereof, which are prepared by the process of the invention.

N-[N'-(2-Aminoethyl)-2-aminoethyl]-3-aminopropyltrimethoxysilane (DYNASYLAN® TRIAMO) is preferably employed as a compound of formula IIIa in the present process.

An example which may be mentioned of a compound having formula IIIb is

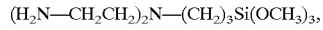

"Bis-product" in the context of the present invention is understood to mean those compounds having formula IIIc, such as, for example, the formula $(H_3CO)_3Si(CH_2)_3NH(CH_2)_2NH(CH_2)_2NH(CH_2)_3Si(OCH_3)_3$.

However, a mixture of triaminoalkyl-functional alkoxysilanes can also be employed in the process of the invention.

Tridecafluoro-1,1,2,2-tetrahydrooctyltrimethoxysilane or tridecafluoro-1,1,2,2-tetrahydrooctyltriethoxy-silane (DYNASYLAN® F8261) is preferably employed as the fluoroalkylalkoxysilane of formula IV in the present process. However, mixtures of several fluoroalkylalkoxysilanes can also be employed.

The alkoxysilanes which are employed in the present process preferably include methoxy- and ethoxysilanes. If an alcohol is added during the process, methanol or ethanol can accordingly be used.

A protonic acid or a mixture of protonic acids is particularly suitable as the catalyst. Thus, for example, formic acid, acetic acid and hydrogen chloride can be employed in the process of the invention. These acids can furthermore also be used to adjust the pH of the composition of the invention.

In the process according to the invention, i) at least one triaminosilane of formulae IIIa to IIIc and ii) at least one fluoroalkylsilane of formula IV are employed in a molar ratio of i/ii≧0.29, preferably 0.3 to 2, particularly preferably 0.33 to 0.5.

The concentration of the organosiloxanes in the aqueous solution of the invention is furthermore suitably adjusted to an active compound content of <50% by weight. An active compound content above 50% by weight can lead to gel formation or severe clouding.

In particular, the content of organosiloxane in the composition of the invention is 0.005 to 40% by weight, preferably 0.01 to 20% by weight, particularly preferably 0.05 to 15% by weight, especially preferably 0.1 to 5% by weight.

The process of the invention is in general conducted so that aminoalkylalkoxysilanes of formulae IIIa to IIIc and fluoroalkylalkoxysilanes of formula IV are mixed. An alcohol is added if desired, and the components are hydrolyzed together and subjected to cocondensation. The alcohol, including the hydrolysis alcohol, is then removed by distillation. Mixing of the alkoxysilanes can take place over a temperature range from the solidification point to the boiling point of the silanes employed. As a rule, water is added in excess to the silane mixture in order to conduct hydrolysis. Hydroxyl-functional organosiloxanes are as a rule obtained by this procedure. However, the hydrolysis or cocondensation can also be conducted with a stoichiometric amount or a stoichiometrically deficient amount of water. If the amount of water added during the reaction is limited to less than 3 mol of water per mol of Si compound employed, substantially alkoxy-containing organosiloxanes of the invention can be prepared. The organosiloxanes of the invention are usually obtained as a mixture in the reaction.

The reaction of the invention is, in general, conducted at a temperature in the range of 0 to 100° C. The reaction of the invention is suitably conducted at a pH of 4 to 12. The hydrolysis preferably takes place at a temperature of <100° C., particularly preferably at <90° C., and especially preferably at <60° C. A good thorough mixing, for example by stirring, is as a rule ensured. The reaction described can furthermore be conducted in the presence of a catalyst.

As a rule, in the process of the invention the alcohol or hydrolysis alcohol is removed by distillation, the distillation preferably being conducted at a temperature of <90° C., particularly preferably at <60° C., and suitably under reduced pressure, since this protects the product. The content of alcohol in the composition is suitably lowered here to less than 5% by weight, preferably to less than 1% by weight, particularly preferably to less than 0.5% by weight.

The distillation can advantageously be conducted in a distillation column and can be continued until no further alcohol can be detected at the top of the column, where the desired product is obtained at the bottom and can be further worked-up, if appropriate. If suspended matter is formed, it can be removed from the product by means of filtration, sedimentation, centrifugation or similar such standard processes.

The composition of the invention can be applied from a 50% strength solution or a dilute solution. Water, for example, can be used as the diluent. In principle, however, the composition of the invention can also be diluted with a corresponding alcohol.

The present invention also relates to compositions which comprise the organosiloxanes of the invention, for example, but not exclusively, those which are employed for hydrophobicizing and/or oleophobicizing surfaces, for "anti-graffiti" applications, for "easy-to-clean" applications, to name only a few.

Compositions of the invention can thus be used in an outstanding manner as compositions for hydrophobicizing and/or oleophobicizing surfaces, as building protection compositions, as compositions for treatment of concrete, naturally occurring mineral substances and glazed and non-glazed ceramic products, as an additive in formulations for surface treatment, for "anti-graffiti" applications and in compositions for "anti-graffiti" applications, for "easy-to-clean" applications and in compositions for "easy-to-clean" applications, as water-soluble adhesion promoters, as a constituent in coating systems and in anticorrosion compositions, for biocidal treatment of surfaces, for treatment of wood, for treatment of leather, leather products and furs, for treatment of glass surfaces, for treatment of plateglass, for treatment of surfaces of plastics, for the preparation of pharmaceutical and cosmetic products, for modification of glass and mineral surfaces and glass and mineral fiber surfaces, for production of artificial stones, for wastewater treatment, for surface modification and treatment of pigments and as a constituent in paints and coatings.

Having now generally described this invention, a further understanding can be obtained by reference to certain specific Examples which are provided herein for purposes of illustration only and are not intended to be limiting unless otherwise specified.

EXAMPLES

Example 1

Preparation of a water-soluble condensate of DYNASYLAN® TRIAMO and DYNASYLAN® F 8261 in a molar ratio of 1:3.

Apparatus

Heatable stirred reactor with a distillation device, internal thermometer and metering device.

Statement of amounts

Starting substances:

| | | |
|---|---|---|
| wt. (DYNASYLAN® TRIAMO) | = 26.5 g | 0.1 mol |
| wt. (DYNASYLAN® F 8261) | = 153.0 g | 0.3 mol |
| wt. (ethanol) | = 60.0 g | |
| wt. (water) | = 10.9 g | 1.5 mol/mol Si(prehydrolysis) |
| wt. (formic acid) | = 16.3 g | 0.3 mol (Biesterfeld, 85%) |
| wt. (water) | = 860.0 g | |

-continued

| Final weights: | |
|---|---|
| wt. (distillate) | = 113.0 g |
| wt. (product) | = 1020.0 g |

Procedure

A 26.5 g amount of TRIAMO, 153.0 g of F 8261 and 60 g of ethanol are initially introduced into the reaction vessel and are stirred under reflux (about 80° C.) for 2 hours. The water for the pre-hydrolysis is then metered in at about 50° C. The reaction mixture is hydrolyzed under reflux at about 78° C. for 8 hours. Thereafter, 16.3 g of formic acid (85%) are metered in at about 50° C. and 860 g of water are added. Thereafter, the product is slightly cloudy.

The alcohol formed upon hydrolysis and the 60 g of ethanol are removed by distillation in vacuo.

Pressure: 160–130 mbar

Internal temperature: 48–50° C.

Analysis of the product by means of 29-Si-NMR analysis gave:

12.9 mol % of Si—monomeric silane (triamino-functional) and M structures (triamino-functional)

9.2 mol % of Si—M structures (fluoroalkyl-functional) and D structures (triamino-functional), 68.1 mol % of Si—D structures (fluoroalkyl-functional) and T structures (triamino-functional).

An average particle size $D_{50}$ of 0.0374 µm (laser light scattering) was determined.

Example 2

The product prepared as described in Example 1 is diluted with water to a concentration of the fluoroalkyltrialkoxysilane originally employed of:

a) 1%, b) 0.1%, c) 0.05%.

For comparison, a cocondensate as described in EP 0 846 716 is prepared from aminopropyltriethoxysilane and DYNASYLAN® F 8261, cf. Example 2 in EP 0 846 716, and is diluted with water to the same fluorosilane content: solutions d), e), f).

Testing on a Porous Mineral Substrate

Lime sandstone test specimens with an edge length of about 10 cm are immersed in the abovementioned solutions for in each case for 10 seconds. After drying in air for about 1 hour, the test specimens are tested comparatively for their liquid-repellent properties with respect to water and a mineral oil (Kaydol, CAS 8012-95-1).

The liquid-repellent properties with respect to water are excellent in all cases (a–f). However, the roll-off angle, which is the angle of inclination necessary to cause a drop of water of defined size to roll off; visual test: the lower the roll-off angle the better the liquid-repellent properties) is significantly lower (that is to say better) with a), b) and c) than with the corresponding comparison solutions d), e) and f). The differences become particularly clear with respect to the oleophobic properties. A drop of a mineral oil (Kaydol) applied to the surface of the test specimen leaves behind no stain after an action time of 30 seconds in the case of a) and b), and a slight formation of a stain is observed in the case of c), which indicates the start of penetration of the oil into the porous mineral test specimen. In the case of d), a slight formation of a stain is observed with the same procedure, and in the case of e) and f) severe staining is observed and, respectively, almost complete absorption of the oil drop is observed.

Result: The formulations of the invention produce better hydrophobic and oleophobic properties on porous, mineral substrates than comparable products of the prior art.

Testing on Glass

Microscope slides of glass (about 76×26 mm, cleaned ready to use, Menzel-Gläser, Article No. 01 1101) are in each case immersed for 1 minute in solution a) or d). After drying, the static contact angle with respect to water is determined by the method described in DIN EN 828.

The glass plate treated with solution a) shows a contact angle of 104°, and the glass plate treated with solution d) shows a contact angle of only 87°. Non-treated glass plates show a contact angle of <30°.

The product from Example 1 of the invention accordingly also has better liquid-repellent properties on smooth surfaces (glass) compared with a comparable product of the prior art.

Example 3

Preparation of a water-soluble condensate of DYNASYLAN® TRIAMO, DYNASYLAN® F 8261 and hexedecyltrimethoxysilane (DYNASYLAN® 9116) in a molar ratio of 1:2:1.

Apparatus

Heatable stirred reactor with a distillation device, internal thermometer, metering device.

Statement of Amounts

Starting substances

| | | | |
|---|---|---|---|
| wt. (DYNASYLAN® TRIAMO) | = 53 g | 0.02 mol | |
| wt. (DYNASYLAN® F 8261) | = 20.4 g | 0.04 mol | |
| wt. (DYNASYLAN® 9116) | = 3.5 g | 0.02 mol | |
| wt. (ethanol) | = 12.0 g | | |
| wt. (water) | = 2.16 g | | |
| wt. (formic acid) | = 3.2 g | | (Biesterfeld, 85%) |
| wt. (water) | = 170.0 g | | |

Final weights wt.(distillate)=97.9 g wt.(product)=118.5 g

Procedure

TRIAMO, F 8261 and ethanol are initially introduced into the reaction vessel and are stirred under reflux (about 80° C.) for 2 hours. The water for the pre-hydrolysis is then metered in at about 50° C. The reaction mixture is hydrolyzed under reflux (about 78° C.) for about 8 hours. Thereafter, the formic acid (85%) is metered in at about 50° C. and the remaining water is added. Thereafter, the product is slightly cloudy.

The hydrolysis alcohol formed and the ethanol additionally added are removed by distillation in vacuo.

Pressure: 160–130 mbar

Internal temperature: 48–50° C.

The resulting product is slightly cloudy and miscible with water in all proportions.

A 93.33 g amount of water is added to 6.67 g of the product and the mixture is applied to a lime sandstone surface. After drying, excellent liquid-repellent properties with respect to water can be observed.

The disclosure of German priority Application No. 19955047.6 filed Nov. 15, 1999 is hereby incorporated by reference into the present application.

Obviously, numerous modifications and variations of the present invention are possible in light of the above teachings. It is, therefore, to be understood that within the scope of the appended claims, the invention may be practiced otherwise than as specifically described herein.

What is claimed as new and is intended to be secured by Letters Patent is:

1. An organosiloxane which has at least one triamino group of formula I:

$$[NH_x(CH_2)_aNH_y(CH_2)_bNH_z]- \qquad (I)$$

which is bonded to at least one silicon atom via at least one N-bonded alkylene group having 1 to 4 C atoms, a and b are identical or different and are each an integer ranging from 1 to 6, x is 0 or 1 or 2, y is 0 or 1, z is 0 or 1 or 2, with the proviso that $(x+y+z) \leq 4$, and at least one Si—C-bonded fluoroalkyl group of formula II:

$$F_3C(CF_2)_r(CH_2)_s- \qquad (II)$$

wherein r is 0 or an integer ranging from 1 to 18 and s is 0 or 2.

2. A composition which comprises at least one organosiloxane containing hydroxyl groups and/or alkoxy groups and water, wherein the organosiloxane carries at least one triamino group of formula I:

$$[NH_x(CH_2)_aNH_y(CH_2)_bNH_z]- \qquad (I)$$

which is bonded to at least one silicon atom via at least one N-bonded alkylene group having 1 to 4 C atoms, a and b are identical or different and are each an integer from 1 to 6, x is 0 or 1 or 2, y is 0 or 1, z is 0 or 1 or 2, with the proviso that $(x+y+z) \leq 4$, and at least one Si—C-bonded fluoroalkyl group of formula II:

$$F_3C(CF_2)_r(CH_2)_s- \qquad (II)$$

wherein r is 0 or an integer ranging from 1 to 18 and s is 0 or 2.

3. The composition as claimed in claim 2, wherein the molar ratio of the groups of formulae I and II in the organosiloxane and/or in the organosiloxane mixture is $1:\leq 3.5$.

4. The composition as claimed in claim 2, wherein the content of organosiloxane ranges from 0 005 to 40% by weight, based on the composition.

5. The composition as claimed in claim 2, which has a pH of less than 11.

6. The composition as claimed in claim 2, which has an alcohol content of less than 5% by weight.

7. A process for the preparation of an organosiloxane-containing composition as claimed in claim 1, which comprises i) mixing at least one aminoalkylalkoxysilane of formula IIIa $$NH_2(CH_2)_2NH(CH_2)_2NH(CH_2)_3Si(R')_j(OR)_{(3-j)} \qquad (IIIa),$$

wherein R and R' are identical or different and are each a linear or branched alkyl group having 1 to 4 C atoms and j is 0 or 1, and/or of formula IIIb:

$$[NH_2(CH_2)_2]_2N(CH_2)_3Si(R')_k(OR)_{(3-k)} \qquad (IIIb)$$

wherein R and R' are identical or different and each is a linear or branched alkyl group having 1 to 4 C atoms and k is 0 or 1, and/or a bis-product or a mixture of bis-products of formula IIIc:

$$[NH_x(CH_2)_aNH_y(CH_2)_bNH_z]\cdot[(CH_2)_cSi(R')_d(OR)_{(3-d)}]_e \qquad (IIIc)$$

wherein R and R' are identical or different and are each a linear or branched alkyl group having 1 to 4 C atoms, a is an integer from 1 to 6, b is 1, 2, 3, 4, 5 or 6, c is 1, 2, 3 or 4, d is 0 or 1, e is 1, 2, 3, 4 or 5, x is 0 or 1 or 2, y is 0 or 1, z is 0 or 1 or 2, with the proviso that $(x+y+z) \leq 4$, such that when e is 5, then $(x+y+z)=0$; when e=4, then $(x+y+z)=1$; when e is 3, then $(x+y+z)=2$; when e=2, then $(x+y+z)=3$; and when e=1, then $(x+y+z)=4$; and ii) at least one fluoroalkylalkoxysilane of formula IV:

$$F_3C(CF_2)_r(CH_2)_sSi(R'')_t(OR)_{(3-t)} \qquad (IV)$$

wherein r is 0 or an integer ranging from 1 to 18, s is 0 or 2 and t is 0 or 1, and R and R" are identical or different and are each a linear or branched alkyl group having 1 to 4 C atoms;

adding water, a water/alcohol mixture or a combination thereof to the mixture;

reacting the mixed at least one aminoalkylalkoxysilane of formulas (IIIa, b and c), and fluoroalkylalkoxysilane of formula (IV) in the aqueous mixture; and optionally completely or partly removing the alcohol.

8. The process as claimed in claim 7, wherein i) at least one aminoalkylalkoxysilane of formulae IIIa to IIIc and ii) at least one fluoroalkylalkoxysilane of formula IV are employed in a molar ratio of $i/ii \geq 0.29$.

9. The process as claimed in claim 7, which further comprises a $C_1$- to $C_{16}$-alkylalkoxysilane as a reactant with components i) and ii).

10. The process as claimed in claim 7, wherein alcohol is added to the mixture of components (i) and (ii) before the reaction commences.

11. The process as claimed in one claim 7, wherein the reaction is conducted at a temperature of <100° C.

12. The process as claimed in one claim 7, wherein the reaction is conducted in the presence of a protonic acid as a catalyst.

13. The process as claimed in claim 7, wherein the reaction is conducted at a pH of 4 to 12.

14. The process as claimed in claim 7, wherein the alcohol is removed from the product mixture obtained by the reaction, down to a content of less than 5% by weight.

15. The process as claimed in claim 13, wherein, after removal of the alcohol, the product mixture is brought to a pH of <12 by addition of an inorganic or organic acid.

16. The process as claimed in claim 12, wherein hydrogen chloride, acetic acid or formic acid is employed as the catalyst, which also enables adjustment of the pH of the reaction mixture.

17. A composition prepared by the process of claim 7.

18. An organosiloxane-containing composition prepared by the process of claim 7.

19. An organosiloxane-containing composition which comprises an organosiloxane as claimed in claim 1.

20. A method of treating surfaces, comprising:

applying the organosiloxane as claimed in claim 1 to surfaces to hydrophobicize and/or to oleophobicize the surfaces.

21. A method of preparing a surface treatment formulation, comprising:

mixing the components of a surface treatment formulation, one of which is the organosiloxane of claim 1, thereby preparing said surface treatment formulation.

22. A method of treating surfaces to achieve a biocidal effect, comprising:

applying the organosiloxane of claim 1 to surfaces of wood, leather and furs.

23. A method of treating surfaces, comprising:

applying the organosiloxane of claim 1 to glass surfaces, plateglass and plastics.

* * * * *